United States Patent
Kato et al.

(10) Patent No.: US 6,921,883 B2
(45) Date of Patent: Jul. 26, 2005

(54) GAS SENSOR AND METHOD OF HEATING THE SAME

(75) Inventors: Nobuhide Kato, deceased, late of Ama-gun (JP); by Kimie Kato, legal representative, Ama-gun (JP); Takeya Miyashita, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 483 days.

(21) Appl. No.: 10/092,389

(22) Filed: Mar. 6, 2002

(65) Prior Publication Data

US 2002/0139671 A1 Oct. 3, 2002

(30) Foreign Application Priority Data

Mar. 9, 2001 (JP) ........................... 2001-066719

(51) Int. Cl.[7] .............................................. H05B 1/02
(52) U.S. Cl. ...................... 219/494; 219/497; 219/544; 204/424; 123/179.1
(58) Field of Search .................. 219/482, 488, 219/490, 494, 497, 505, 520, 538, 541, 542, 544; 123/179.1, 685, 697; 700/207; 204/424, 426

(56) References Cited

U.S. PATENT DOCUMENTS

| | | | | |
|---|---|---|---|---|
| 3,946,198 A | * | 3/1976 | Foote | ........................ 219/497 |
| 4,404,462 A | * | 9/1983 | Murray | ........................ 219/497 |
| 4,655,182 A | * | 4/1987 | Nakano et al. | .......... 123/179.1 |
| 4,883,947 A | * | 11/1989 | Murase et al. | ............... 219/541 |
| 5,111,792 A | * | 5/1992 | Nagai et al. | ................. 123/685 |
| 5,719,778 A | * | 2/1998 | Suzumura et al. | .......... 700/207 |
| 6,258,232 B1 | | 7/2001 | Hasegawa et al. | |

FOREIGN PATENT DOCUMENTS

| | | |
|---|---|---|
| DE | 198 60 104 A1 | 7/1999 |
| EP | 0 695 983 A2 | 2/1986 |
| JP | 63-38154 A | 2/1988 |
| JP | 64-39545 A | 2/1989 |
| JP | 1-277751 A | 11/1989 |
| JP | 2-1543 A | 1/1990 |

\* cited by examiner

*Primary Examiner*—Tu Hoang
(74) *Attorney, Agent, or Firm*—Burr & Brown

(57) ABSTRACT

Temperature of a heater is controlled by switching an increasing rate of a resistance value of heating unit of the heater. During a period T1 from a time point when heating of the heater is started until the resistance value of the heating unit reaches a reference value, the increasing rate is changed in multiple heating stages. In this manner, the temperature and the resistance value of the heating unit are increased. During a period T2 from a time point when the resistance value of the heating unit reaches the reference value, feedback control is performed such that the resistance value is kept at the reference value as a target value.

9 Claims, 16 Drawing Sheets

GAS SENSOR AND METHOD OF HEATING THE SAME

BACKGROUND OF THE INVENTION

1. Field of the Invention

The present invention relates to a gas sensor having a ceramic substrate in which a heater for heating the gas sensor is embedded. Further, the present invention relates to a method of heating the gas sensor. The gas sensor measures oxides such as NO, $NO_2$, $SO_2$, $CO_2$, and $H_2O$ and inflammable gases such as CO and $C_nH_m$ in atmospheric air and exhaust gas discharged from vehicles.

2. Description of the Related Art

Various measuring systems and apparatuses for measuring concentration of gas components in a measurement gas have heretofore been proposed.

For example, according to a method of measuring concentration of NOx in a measurement gas such as exhaust gas, Nox-reducing ability of Rh is utilized. A sensor having a Pt electrode and an Rh electrode formed on an oxygen ion-conductive solid electrolyte such as zirconia is used to measure an electromotive force generated between the electrodes.

However, the sensor is likely to be affected by noises, since the electromotive force changes significantly depending on the change of oxygen concentration in the measurement gas (exhaust gas), and the electromotive force does not change significantly depending on the change of NOx concentration. Further, in order to effectively utilize the NOx-reducing ability of Rh, reducing gases such as CO are required. In general, when the amount of fuel is not enough in combustion, a large amount of NOx is produced. Under the condition, the amount of CO produced in the combustion is small in comparison to the amount of NOx. Therefore, it is not possible to measure the concentration of NOx.

Japanese Laid-Open Patent Publication Nos. 63-38154 and 64-39545 disclose a method of measuring the concentration of NOx. In the method, a pair of electrochemical pumping cells and a sensor cell comprising Pt electrodes and oxygen-ion conductive solid electrolytes and another pair of electrochemical pumping cells and a sensor cell comprising Rh electrodes and an oxygen-ion conductive solid electrolyte are used. The concentration of NOx is measured based on the difference between pumping current values.

Further, according to Japanese Laid-Open Patent Publication Nos. 1-277751 and 2-1543, a pair of sensors each comprising an electrochemical pumping cell and a sensor cell are used. One of the sensors measures a limiting pumping current value at a partial pressure of oxygen in which NOx is not reduced. The other sensor measures a limiting pumping current value at a partial pressure of oxygen in which NOx is reduced. The difference between these limiting pumping current values is calculated. Alternatively, one sensor comprising an electrochemical pumping cell and a sensor cell is used. The sensor selectively measures the limiting pumping current at a partial pressure of oxygen in which NOx is not reduced, or measures the limiting pumping current at a partial pressure of oxygen in which NOx is reduced. The difference between these limiting pumping current values is calculated.

In automobile applications, the temperature of the exhaust gas changes significantly. Therefore, a heater is embedded in the gas sensor so that the operation of the gas sensor is not affected by the change in the temperature of the exhaust gas.

When the heater is turned on, the temperature of the heater is controlled by (1) performing a PID control, (2) controlling the electric current so that the voltage applied to the heater is increased, and (3) applying ramp voltage or staircase voltage to the heater.

SUMMARY OF THE INVENTION

An object of the present invention is to provide a gas sensor and a method of heating the gas sensor in which the control method of the heater is improved so that the gas sensor can be heated highly accurately and reliably. According to the present invention, a method of heating a gas sensor including a ceramic substrate and a heater embedded in the substrate is performed by controlling the temperature of the heater. The heating method comprises the steps of:

increasing the temperature of the heater rapidly when the temperature of the substrate is low; and increasing the temperature of the heater slowly when the temperature of the substrate is high.

In this method, when the control mode of the heater is switched to feedback control, temperature of the substrate is not increased excessively rapidly. Therefore, it is possible to prevent formation of cracks in the substrate.

Preferably, the temperature of the heater is increased slowly when the temperature of the substrate is equal to or greater than 600 degrees centigrade. Specifically, it is preferable that the temperature of the heater is increased at a speed equal to or less than 40 degrees centigrade/sec. when the temperature of the substrate is equal to or greater than 600 degrees centigrade. Preferably, the temperature of the heater is increased rapidly when the temperature of the substrate is equal to or less than 500 degrees centigrade. Specifically, the temperature of the heater is increased at a speed greater than 20 degrees centigrade/sec., equal to or less than 100 degrees centigrade/sec. when the temperature of the substrate is equal to or less than 500 degrees centigrade.

Preferably, voltage applied to the heater changes depending on the time passed for increasing the temperature of the heater, according to an exponential curve of a first order time-lag function (for example, $y=1-e-at$).

Preferably, the heater has a heating unit, and a resistance of the heating unit of the heater is measured and controlled for increasing the temperature of the heater so that the temperature of the heater can be controlled easily.

Further, according to the present invention, a gas sensor has a ceramic substrate and a heater embedded in the substrate. The gas sensor comprises:

means for measuring a resistance of a heating unit of the heater; and means for controlling a rate of increasing the resistance of the heating unit per unit time.

Preferably, the resistance measuring means comprises at least one measuring lead for measuring the resistance of the heating unit.

The above and other objects, features, and advantages of the present invention will become more apparent from the following description when taken in conjunction with the accompanying drawings in which a preferred embodiment of the present invention is shown by way of illustrative example.

DETAILED DESCRIPTION OF THE INVENTION

An embodiment of a gas sensor 10 and a method of heating the gas sensor 10 according to the present invention will be described with reference to FIGS. 1 to 16. The gas sensor 10 measures oxides such as NO, $NO_2$, $SO_2$, $CO_2$, and $H_2O$ and inflammable gases such as CO and $C_nH_m$ in the exhaust gas discharged from vehicles and atmospheric air, for example.

Figure 1:
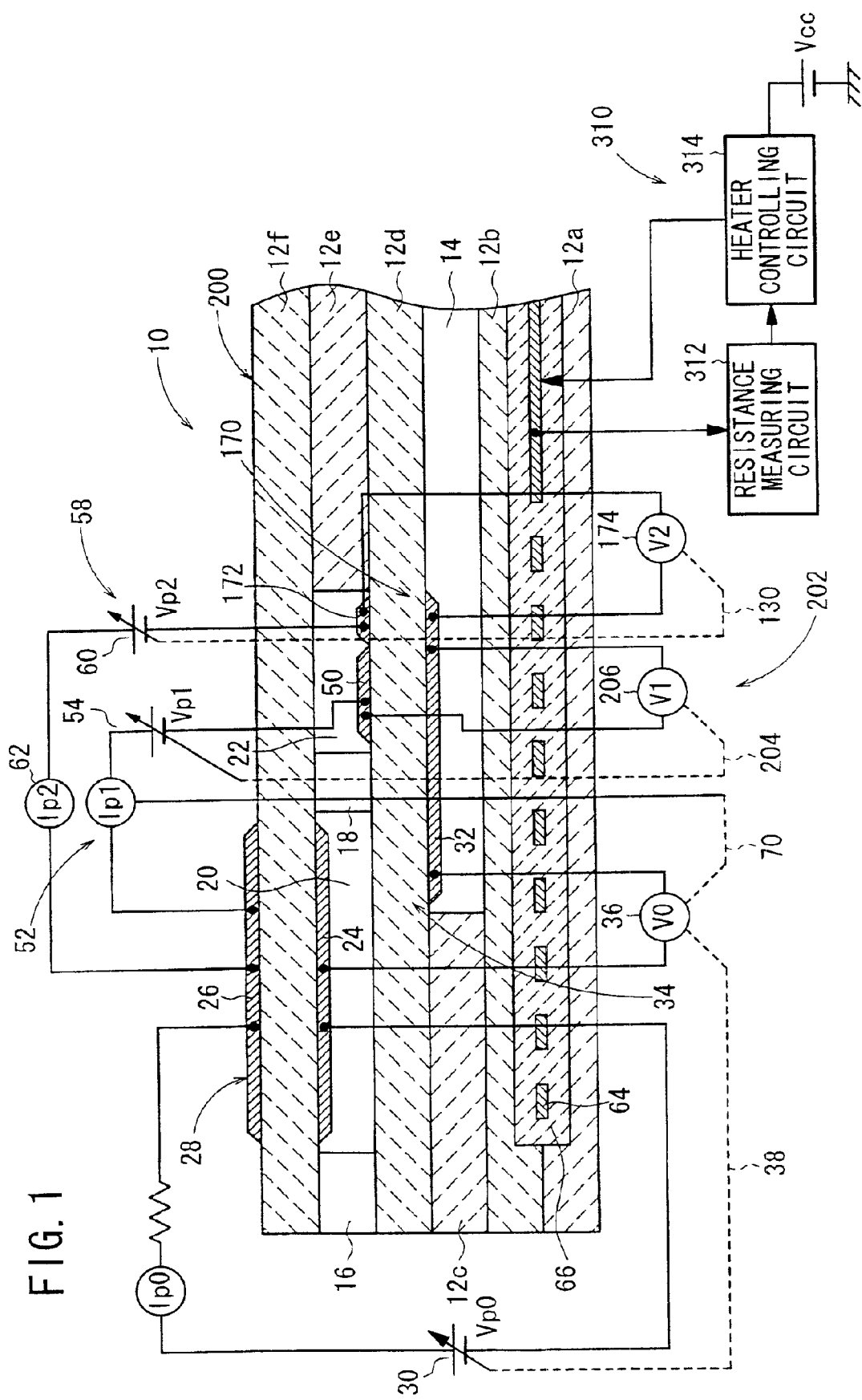
FIG. 1 is a view showing a gas sensor according to an embodiment of the present invention.

As shown in FIG. 1, the gas sensor 10 according to the present embodiment comprises a substrate 200. The substrate 200 is made up of six stacked solid electrolyte layers 12a to 12f, for example. The solid electrolyte layers 12a to 12f are formed of oxygen ion-conductive solid electrolytes of ceramics such as $ZrO_2$.

First and second layers from the bottom are first and second substrate layers 12a, 12b. Third and fifth layers from the bottom are first and second spacer layers 12c, 12e. Fourth and sixth layers from the bottom are first and second solid electrolyte layers 12d, 12f.

The first spacer layer 12c is stacked oh the second substrate layer 12b. The first solid electrolyte layer 12d is stacked on the first spacer layer 12c. The second solid spacer layer 12e is stacked on the first solid electrolyte layer 12d. The second solid electrolyte layer 12f is stacked on the second solid spacer layer 12e.

A space for introducing a reference gas such as atmospheric air used as a reference for measuring oxides (reference gas-introducing space 14) is formed between the second substrate layer 12b and the first solid electrolyte layer 12d. The reference gas-introducing space 14 is surrounded by a lower surface of the first solid electrolyte layer 12d, an upper surface of the second substrate layer 12b, and side surfaces of the first spacer layer 12c.

The second spacer layer 12e is interposed between the first and second solid electrolyte layers 12d, 12f. Further, first and second diffusion rate-determining sections 16, 18 are interposed between the first and second solid electrolyte layers 12d, 12f.

Further, a first chamber 20 for adjusting the partial pressure of oxygen in a measurement gas is formed by a lower surface of the second solid electrolyte layer 12f, side surfaces of the first and second diffusion rate-determining sections 16, 18, and an upper surface of the first solid electrolyte layer 12d. A second chamber 22 for finely adjusting the partial pressure of oxygen in the measurement gas and measuring oxides, for example, nitrogen oxides (NOx) in the measurement gas is formed by a lower surface of the second solid electrolyte layer 12f, a side surface of the second diffusion rate-determining section 18, a side surface of the second spacer layer 12e, and an upper surface of the first solid electrolyte layer 12d.

The first chamber 20 communicates with an external space via the first diffusion-rate determining section 16, and the first chamber 20 communicates with the second chamber 22 via the second diffusion rate-determining section 18.

The first and second diffusion-rate determining sections 16, 18 have predetermined diffusion resistances to control the introduction of the measurement gas into the first and second chambers 20, 22 respectively. Each of the first and second diffusion-rate determining sections 16, 18 may be formed as a passage composed of, for example, a porous material of $ZrO_2$, or a small hole having a predetermined cross-sectional area so that the measurement gas can be introduced into the first and second chambers 20, 22. Alternatively, each of the first and second diffusion-rate determining sections 16, 18 may be a porous layer or a gap layer formed by printing. The diffusion resistance of the first diffusion-rate determining section 16 may be larger than, equal to, or smaller than the diffusion resistance of the second diffusion-rate determining section 18. However, it is preferable that the diffusion resistance of the second diffusion-rate determining section 18 is larger than the diffusion resistance of the first diffusion-rate determining section 16.

The atmosphere in the first chamber 20 is introduced into the second chamber 22 under the predetermined diffusion resistance via the second diffusion rate-determining section 18.

A substantially rectangular inner pumping electrode 24 composed of a porous cermet electrode is formed on the lower surface of the second solid electrolyte layer 12f at a substantially overall portion in the first chamber 20. An outer pumping electrode 26 is formed on the upper surface of the second solid electrolyte layer 12f oppositely to the inner pumping electrode 24. The inner pumping electrode 24, the outer pumping electrode 26, and the second solid electrolyte layer 12f interposed between the electrodes 24, 26 make up an electrochemical pumping cell, i.e., a main pumping cell 28.

A desired control voltage (pumping voltage) Vp0 is applied between the inner pumping electrode 24 and the outer pumping electrode 26 of the main pumping cell 28 by an external variable power source 30 to allow a pumping current to selectively flow from the outer pumping electrode 24 to the inner pumping electrode 26, or from the inner pumping electrode 26 to the outer pumping electrode 24. Thus, the oxygen in the atmosphere in the first chamber 20 is pumped out to the external space, or the oxygen in the external space is pumped into the first chamber 20.

A reference electrode 32 is formed on the lower surface of the first solid electrolyte layer 12d at a portion exposed to the reference gas-introducing space 14. The inner pumping electrode 24, the reference electrode 32, the second solid electrolyte layer 12f, the second spacer layer 12e, and the first solid electrolyte layer 12d make up an electrochemical pumping cell, i.e., an oxygen partial pressure-measuring cell 34.

An electromotive force (voltage) V0 is generated between the inner pumping electrode 24 and the reference electrode 32 depending on the difference in oxygen concentration between the atmosphere in the first chamber 20 and the reference gas (atmospheric air) in the reference gas-introducing space 14. The oxygen partial pressure-measuring cell 34 measures the electromotive force V0 to measure the partial pressure of oxygen in the atmosphere in the first chamber 20.

The voltage V0 generated between the inner pumping electrode 24 and the reference electrode 32 is an oxygen concentration cell electromotive force generated depending on the difference between the partial pressure of oxygen in the reference gas introduced into the reference gas-introducing space 14 and the partial pressure of oxygen in the measurement gas in the first chamber 20. The voltage V0 is obtained by the Nernst equation which is written as:

$$V0 = RT/4F \times \ln\{P1(O_2)/P0(O_2)\}$$

where R is the gas constant, T is the absolute temperature, F is the Faraday constant, P1 ($O_2$) is the partial pressure of oxygen in the first chamber 20, and P0 ($O_2$) is the partial pressure of oxygen in the reference gas.

The voltage V0 calculated by the Nernst equation is measured by a voltmeter 36 to detect the partial pressure of oxygen.

The value of the partial pressure of oxygen is used to control the pumping voltage Vp0 of the variable power source 30 through a feedback control system 38. The pumping operation of the main pumping cell 28 is controlled so that the partial pressure of oxygen in the atmosphere in the first chamber 20 is low enough to control the partial pressure of oxygen in the second chamber 22. Specifically, the value of the partial pressure of oxygen in the atmosphere in the first chamber 20 is controlled so that NO components to be measured by the gas sensor 10 cannot be reduced substantially in the first chamber 20. The NO components in the first chamber 20 may be reduced partially.

In particular, in the present embodiment, when the amount of oxygen pumped out by the main pumping cell 28 changes, oxygen concentration in the first chamber 20 changes. Thus, the voltage applied between a terminal of the inner pumping electrode 24 and a terminal of the reference electrode 32 changes without any delay (changes in real time). Therefore, parasitic oscillations in the feedback control system 38 are suppressed effectively.

The inner pumping electrode 24 and the outer pumping electrode 26 are composed of an inert material having a low catalytic activity against NOx, for example, NO in the measurement gas introduced in the first chamber 20. The inner pumping electrode 24 and the outer pumping electrode 26 may be composed of a porous cermet containing a metal such as Pt and a ceramics such as $ZrO_2$. The inner pumping electrode 24 needs to be composed of a material having a low reducing ability or no reducing ability against NO components in the measurement gas. For example, it is preferable that the inner pumping electrode 24 is composed of a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the metal components.

As shown in FIG. 1, a substantially rectangular measuring electrode 172 composed of a porous cermet electrode is formed on the upper surface of the first solid electrolyte layer 12d, at a portion in the second chamber 22 and spaced from the second diffusion rate-determining section 18.

The measuring electrode 172, the outer pumping electrode 26, the first solid electrolyte layer 12d, the second spacer layer 12e, and the second solid electrolyte layer 12f between the electrodes 172 and 26, make up a measuring pumping cell 58. The measuring pumping cell 58 pumps out oxygen in the atmosphere in the second chamber 22 to the external space by applying a voltage Vp2 between the measuring electrode 172 and the outer pumping electrode 26. The voltage Vp2 is supplied from a variable power source 60.

The measuring electrode 172, the reference electrode 32, and the first solid electrolyte layer 12d between the electrodes 172 and 32 make up oxygen partial pressure measuring cell 170.

An electromotive force (oxygen concentration cell electromotive force) is generated between the measuring electrode 172 and the reference electrode 32 of the oxygen partial pressure measuring cell 170 depending on the difference in oxygen concentration between the atmosphere around the measuring electrode 172 and the atmosphere around the reference electrode 32.

The electromotive force generated between the measuring electrode 172 and the reference electrode 32 are measured to detect the partial pressure in the atmosphere around the measuring electrode 172, i.e., the partial pressure of oxygen which is generated by reduction or decomposition of measurement gas components (NOx).

The measuring electrode 172 is composed of a porous cermet comprising zirconia as a ceramic and Rh as a metal capable of reducing NOx as the measurement gas components. The measuring electrode 172 functions as a NOx-reducing catalyst for reducing NOx in the atmosphere in the second chamber 22. The pumping current Ip2 which flows under the pumping operation of the measuring pumping cell 58 is measured by an ammeter 62.

A substantially rectangular auxiliary pumping electrode 50 composed of a porous cermet electrode is formed on the upper surface of the first solid electrolyte layer 12d, at a portion in the second chamber 22 adjacent to the measuring electrode 172.

The auxiliary pumping electrode 50, the outer pumping electrode 26, the first solid electrolyte layer 12d, the second spacer layer 12e, and the second solid electrolyte layer 12f between the electrodes 50 and 26 make up an auxiliary pumping cell 52. The auxiliary pumping electrode 50, the reference electrode 32, and the first solid electrolyte layer 12d make up an auxiliary oxygen partial pressure measuring cell 202.

As with the inner pumping electrode 24 of the main pumping cell 28, it is preferable that the auxiliary pumping electrode 50 is composed of a material having a low reducing ability or no reducing ability against NO components in the measurement gas, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the metal components.

The auxiliary pumping cell 52 pumps out oxygen in the atmosphere in the second chamber 22 to the external space by applying an auxiliary voltage Vp1 between the auxiliary pumping electrode 50 and the outer pumping electrode 26. The voltage Vp1 is supplied by a variable power source 54.

As with the oxygen partial pressure measuring cell 170, the auxiliary oxygen partial pressure measuring cell 202 measures the electromotive force (oxygen partial pressure value, potential difference) V1 generated between the auxiliary pumping electrode 50 and the reference electrode 32 based on the difference in the partial pressure of oxygen between the atmosphere in the second chamber 22 and the reference gas (atmospheric air) in the reference gas introducing space 14. The electromotive force V1 is measured by the voltmeter 206. Thus, the partial pressure of oxygen in the atmosphere in the second chamber 22 is measured.

The measured value of the partial pressure of oxygen V1 is used to control the pumping voltage Vp1 of the variable power source 54 through a feedback control system 204. In the second chamber 22, the measurement gas component (NO) is not reduced or decomposed significantly. Under the condition, the pumping voltage Vp1 is controlled so that the partial pressure of oxygen in the atmosphere in the second chamber 22 is low enough to measure the amount of target component (oxygen produced when NO is decomposed by the measuring electrode 172).

Specifically, the voltage value of the variable power source 54 is controlled so that a limiting current is supplied to the auxiliary pumping cell 52. The auxiliary pumping cell 52 does not pump out oxygen produced when NO is decomposed by the measuring electrode 172.

When the amount of oxygen pumped out by the auxiliary pumping cell 52 changes, oxygen concentration in the second chamber 22 changes correspondingly. Thus, the voltage applied between a terminal of the auxiliary pumping electrode 24 and the terminal of the reference electrode 32 changes without any delay (changes in real time). Therefore, parasitic oscillations in the feedback control system 204 are suppressed effectively, and it is possible to control the concentration of oxygen in the second chamber 22 highly accurately.

As described above, the partial pressure of oxygen in the atmosphere in the second chamber 22 is controlled so that the measurement gas component (NO) is not reduced or decomposed significantly. The partial pressure of oxygen is low. Therefore, the measurement of the amount of the target component (oxygen produced when NO is decomposed by the measuring electrode 172) is not affected by the partial pressure of oxygen in the second chamber 22. The main pumping cell 28 of the first chamber 20 decreases the change in the amount of oxygen introduced from the first chamber 20 into the second chamber 22 in comparison with the change in the amount of the measurement gas component. Therefore, the partial pressure of oxygen in the second chamber 22 is finely adjusted at a constant level.

Further, in the gas sensor 10 according to the present embodiment, a heater 64 is embedded between the upper first substrate layer 12a and the lower second substrate layer 12b. The heater 64 is heated when power is supplied to the heater 64 from an external power source.

The heater 64 improves conductivity of oxygen ion. A ceramic layer 66 composed of alumina or the like surrounds upper and lower surfaces of the heater 64 so that the heater 64 is electrically insulated from the substrate layers 12a, 12b.

As shown in FIG. 1, the heater 64 is arranged over the entire areas of the first chamber 20 and the second chamber 22. Thus, the first chamber 20 and the second chamber 22 are heated to a predetermined temperature. Further, each of the main pumping cell 28, the oxygen partial pressure-measuring cell 34, the auxiliary pumping cell 52, the measuring pumping cell 58, and the oxygen partial pressure-measuring cell 170, and the auxiliary oxygen partial pressure-measuring cell 202 are heated, and kept at the predetermined temperature.

Figure 2:
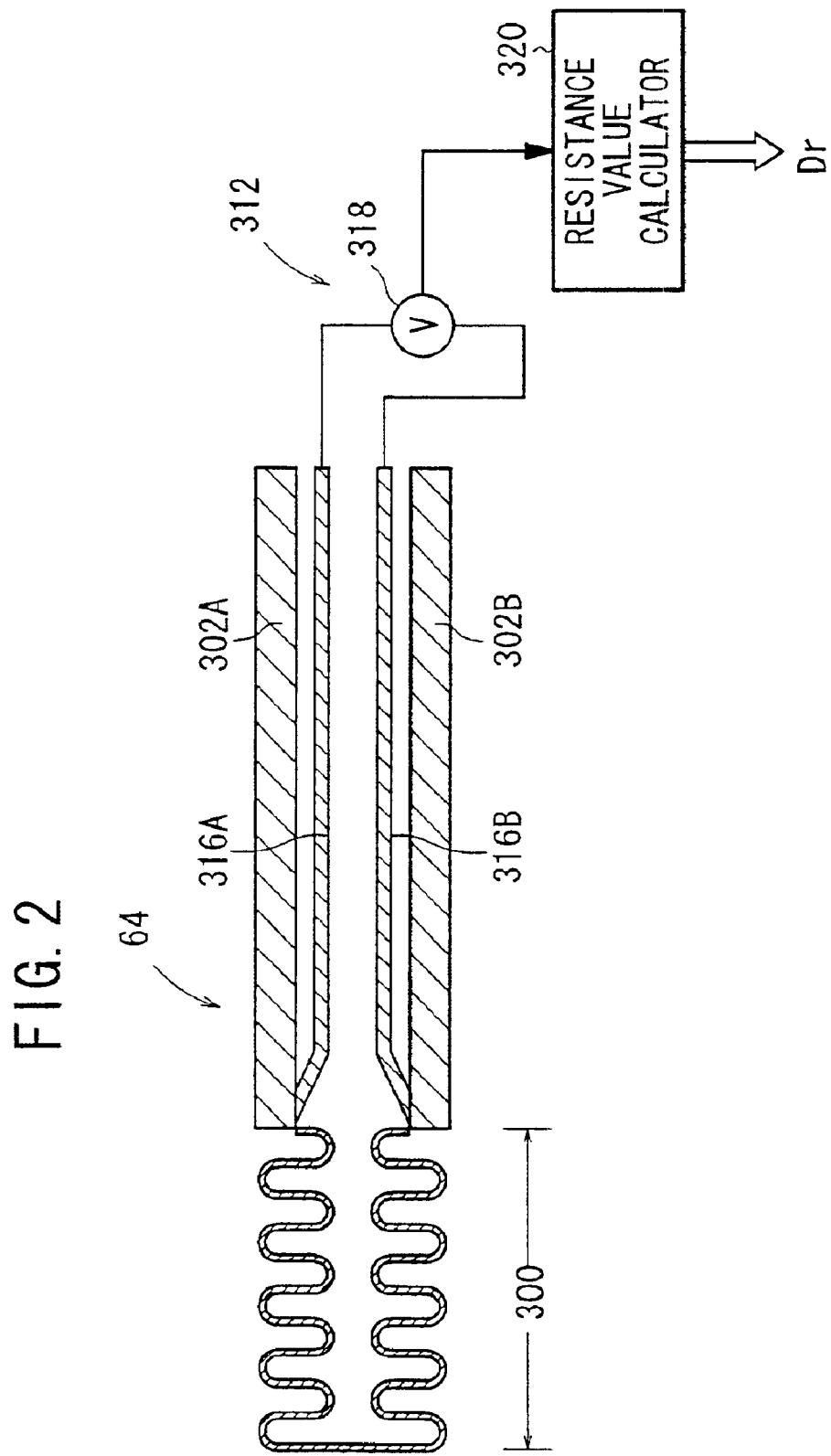
FIG. 2 is a view showing a heater and a resistance measuring circuit of the gas sensor according to the embodiment of the present invention.

As shown in FIG. 2, the heater 64 comprises a heating unit 300, two current leads 302A, 302B extending from terminals of the heater 64 to the outside of the substrate 200, two voltage measuring leads 316A, 316B also extending from the terminals of the heater 64 to the outside of the substrate 200. The current leads 302A, 302B may not be used when one of the voltage measuring leads 316A, 316B functions as the current leads 302A, 302B.

The gas sensor 10 according to the present embodiment comprises an auxiliary control system 70 for correcting control of the feedback control system 38 of the main pumping cell 28 based on the value of pumping current IP1 flowing through the auxiliary pumping cell 52.

The auxiliary control system 70 keeps oxygen concentration in the second chamber 22 at a constant level so as to prevent the measurement accuracy from being adversely affected by the leakage of oxygen due to a large change of oxygen concentration in the measurement gas or by minute decomposition of $H_2O$ in the measurement gas due to the increase of $H_2O$ concentration. Further, the auxiliary control system 70 prevents the measurement accuracy from being affected by the change in temperature and degradation of the main pumping cell 28.

The gas sensor 10 according to the present embodiment comprises a heater control system 310 for controlling supply of electricity to the heater 64 based on the temperature of the substrate 200. The temperature of the substrate 200 is equivalent to the temperature of the heating unit 300. Further, the temperature of the heating unit 300 changes in proportion to the resistance of the heating unit 300.

The heater control system 310 of the gas sensor 10 according to the present embodiment comprises a resistance measuring circuit 312 for measuring a resistance of the heating unit 300, and a heater controlling circuit 314 for controlling supply of electricity to the heater 64 based on the resistance measured by the resistance measuring circuit 312.

The resistance measuring circuit 312 uses the four-terminal method. Specifically, as shown in FIG. 2, the resistance measuring circuit 312 comprises the two voltage measuring leads 316A, 316B, a potentiometer 318, a resistance value calculator 320. The voltage measuring leads 316A, 316B are connected to the opposite terminals of the heating unit 300, and extend to the outside of the substrate 200. The potentiometer 318 is connected to the voltage measuring leads 316A, 316B. The resistance value calculator 320 calculates a resistance value Dr of the heating unit 300 based on the voltage value measured by the potentiometer 318 and a value of the electric current supplied to the heater 64.

Basically, no electric current of the heater 64 is supplied to the two voltage measuring leads 316A, 316B. Therefore, the resistance of the voltage measuring leads 316A, 316B does not affect the measurement. If only one voltage measuring lead is used, the voltage drop of the current lead 302A and the voltage drop of the current lead 302B are considered to be the same in the measurement.

Figure 3:
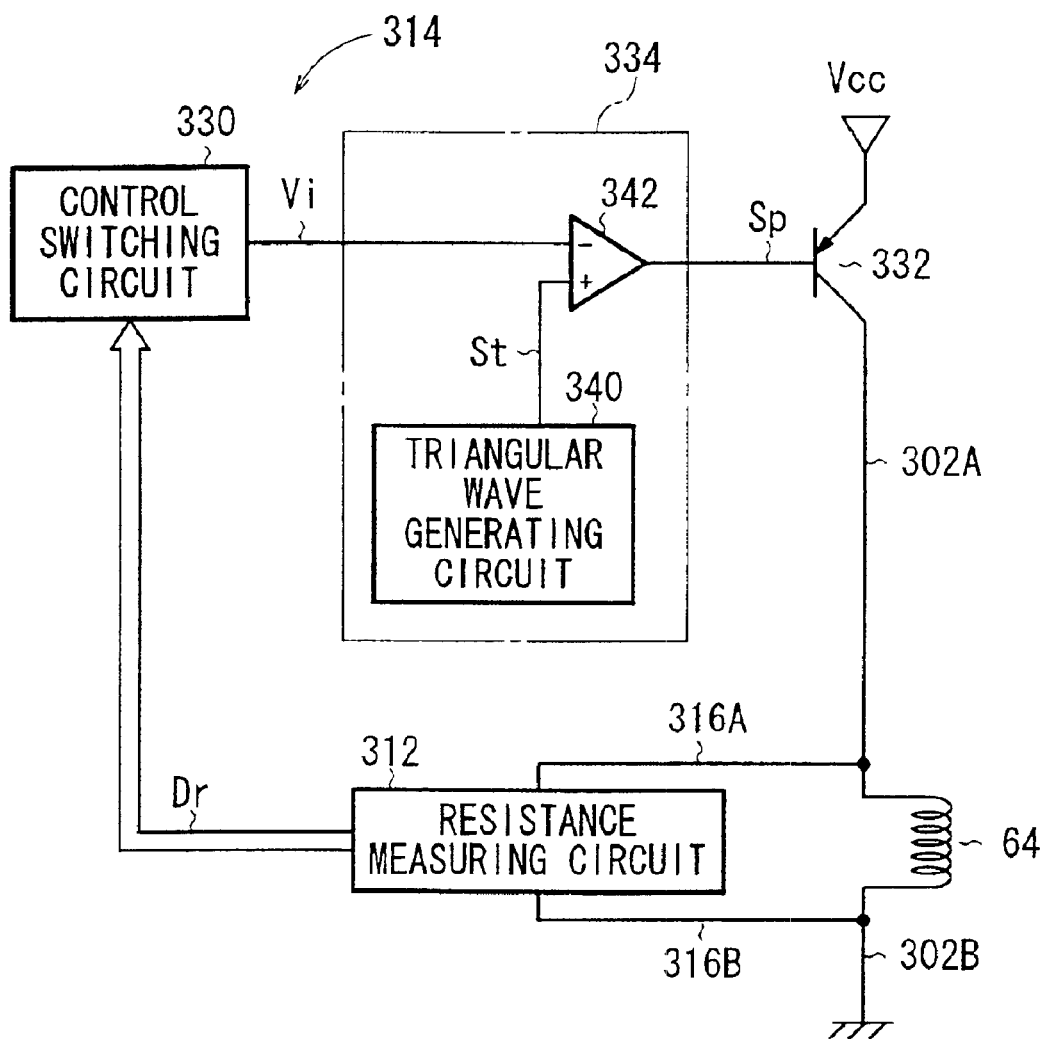
FIG. 3 is a diagram showing a heater controlling circuit of the gas sensor according to the embodiment of the present invention.

As shown in FIG. 3, the heater controlling circuit 314 comprises a control switching circuit 330, a pnp-type power transistor 332, and a pulse width modulating circuit 334. The control switching circuit 330 switches a control mode for controlling the heater 64 based on the resistance value Dr detected by the resistance measuring circuit 312. Further, the control switching circuit 330 outputs a voltage signal (output signal) Vi generated according to the control mode. The pulse width modulating circuit 334 modulates the pulse width of a signal for driving a base of the power transistor 332 (hereinafter simply referred to as the base driving signal Sp).

The pulse width modulating circuit 334 comprises a triangular wave generating circuit 340 and a comparator 342. The triangular wave generating circuit 340 generates a predetermined triangle wave St having a base level −5V and a is peak level +5V, for example. The comparator 342 compares the triangle wave St with the output signal Vi from the control switching circuit 330. According to a circuit arrangement shown in FIG. 3, the output signal Vi from the control switching circuit 330 is inputted to an inverting input terminal of the comparator 342, and the triangle wave St from the triangle wave generating circuit 340 is inputted to a non-inverting input terminal of the comparator 342.

The power transistor 332 has an emitter terminal connected to a power supply Vcc, a base terminal connected to an output terminal of the comparator 342 and a collector terminal connected to the electric current lead 302A of the heater 64. The other electric current lead 302B is grounded.

The power transistor 332 is turned on when a low level signal is supplied from the comparator 342 to the base terminal. Thus, driving current is supplied from the power supply Vcc to the heater 64. The power transistor 332 is turned off when a high level signal is supplied from the comparator 342 to the base terminal. Thus, the supply of the driving current to the heater 64 is stopped.

Figure 4A:
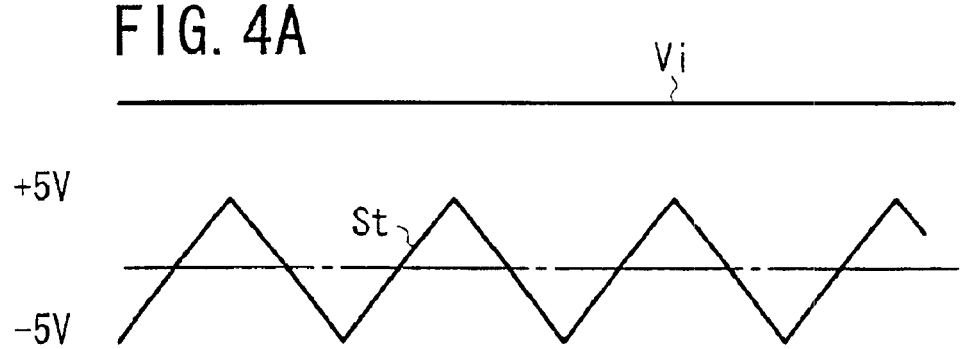
FIG. 4A shows a waveform in which a level of a deviation signal is higher than a peak level of a triangular wave.
Figure 4B:
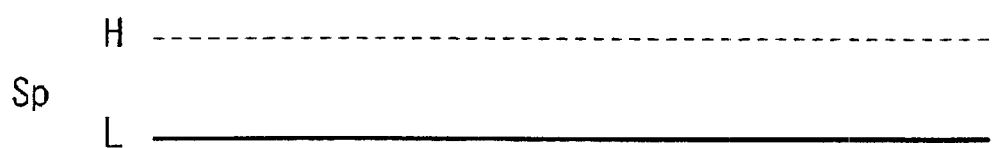
FIG. 4B shows a base-driving signal under the condition of FIG. 4A.
Figure 5A:
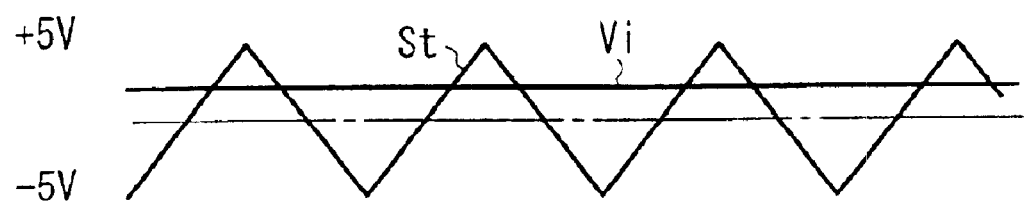
FIG. 5A shows a waveform in which a level of a deviation signal is between a middle level and the peak level of the triangular wave.
Figure 5B:
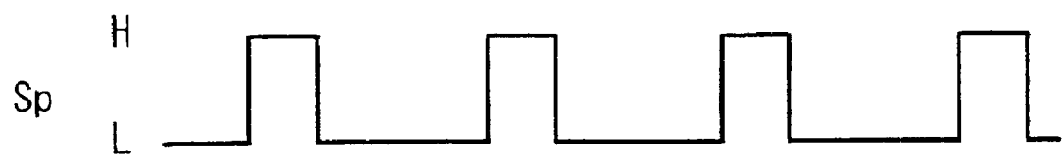
FIG. 5B shows a base-driving signal under the condition of FIG. 5A.
Figure 6A:
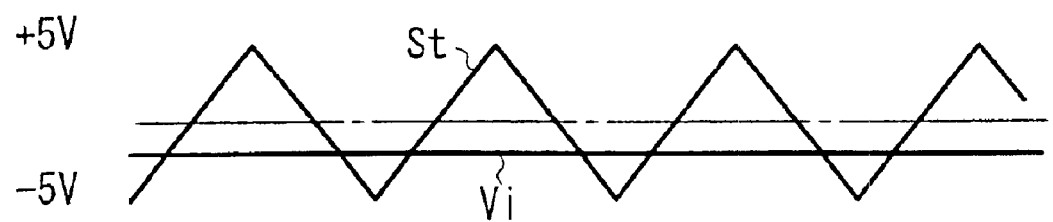
FIG. 6A shows a waveform in which a level of a deviation signal is between the bottom level and the middle level of the triangular wave.
Figure 6B:
FIG. 6B shows a base-driving signal under the condition of FIG. 6A.
Figure 7A:
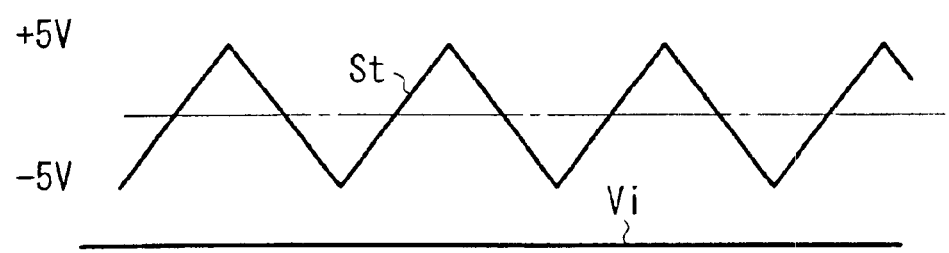
FIG. 7A shows a waveform in which a level of a deviation signal is lower than the bottom level of the triangular wave.
Figure 7B:
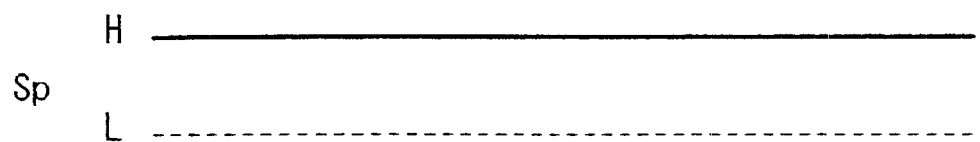
FIG. 7B shows a base-driving signal under the condition of FIG. 7A.

The level of the output signal Vi from the control switching circuit 330 functions as a threshold for the triangle wave St. Specifically, as shown in FIG. 4A, when the level of the output signal Vi is equal to higher than the peak level of the triangle wave St, as shown in FIG. 4B, the low level base driving signal Sp is outputted from the comparator 342 constantly. As shown in FIGS. 5A, 6A, when the level of the output signal Vi is higher than the base level of the triangle wave St and lower than the peak level of the triangle wave St, a base driving signal as shown in FIGS. 5B, 6B is outputted. In FIGS. 5A, 6A, the triangle wave St has high level periods in which the level of the triangle wave St is higher than the level of the output signal Vi, and the triangle wave St has low level periods in which the level of the triangle wave St is lower than the level of the output signal Vi. As shown in FIG. 7A, when the level of the output signal Vi is equal to or lower than the base level of the triangle wave St, a high level base driving signal as shown in FIG. 7B is constantly outputted from the comparator 342.

Next, two example of the control switching circuit 330 will be described with reference to FIGS. 8 to 14.

Figure 8:
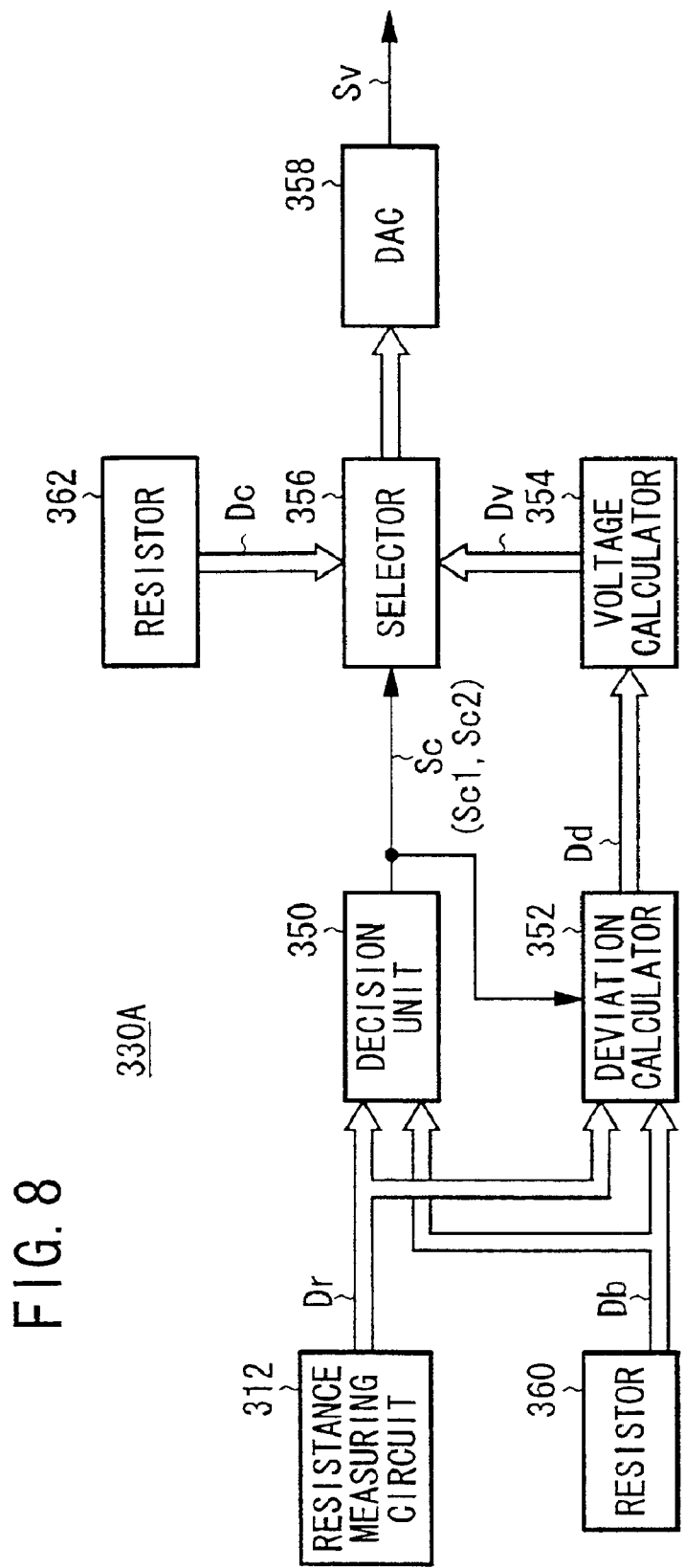
FIG. 8 is a diagram showing an arrangement of a control switching circuit of a first example.

As shown in FIG. 8, a control switching circuit 330A of the first example comprises a decision unit 350, a deviation calculator 352, a voltage calculator 354, a selector 356, and a D/A converter (DAC) 358.

The decision unit 350 compares a resistance value Dr from the resistance measuring circuit 312 with a reference value to output an instruction signal Sc (signal Sc1 for constant voltage control or signal Sc2 for feedback control).

Specifically, the decision unit 350 outputs the instruction signal Sc1 for performing constant voltage control from a time point when heating of the heater 64 is started until the resistance value Dr reaches the reference value Db. The decision unit 350 outputs the instruction signal Sc2 for performing feedback control from a time point when the resistance value Dr reaches the reference value Db.

The deviation calculator 352 is enabled if the instruction signal Sc is the signal Sc2 for feedback control. The deviation calculator 352 calculates the deviation value Dd between the resistance value Dr from the resistance measuring circuit 312 and the reference value Db from a resistor 360. The voltage calculator 354 calculates the voltage Dv to be outputted to the comparator 342 based on the deviation value Dd from the deviation calculator 352.

The selector 356 outputs a constant voltage value Dc corresponding to resistor 362 to the D/A converter 358 if the instruction signal Sc is the signal Sc1 for constant voltage control. The selector 356 outputs the voltage value Dv from the voltage calculator 354 to the D/A converter 358 if the instruction signal Sc is the signal Sc2 for feedback control.

The D/A converter 358 converts the voltage value (constant voltage value Dc or voltage value Dv) into an analog voltage signal Sv, and outputs the voltage signal Sv to the comparator 342 of the pulse width modulation circuit 334.

Figure 9A:
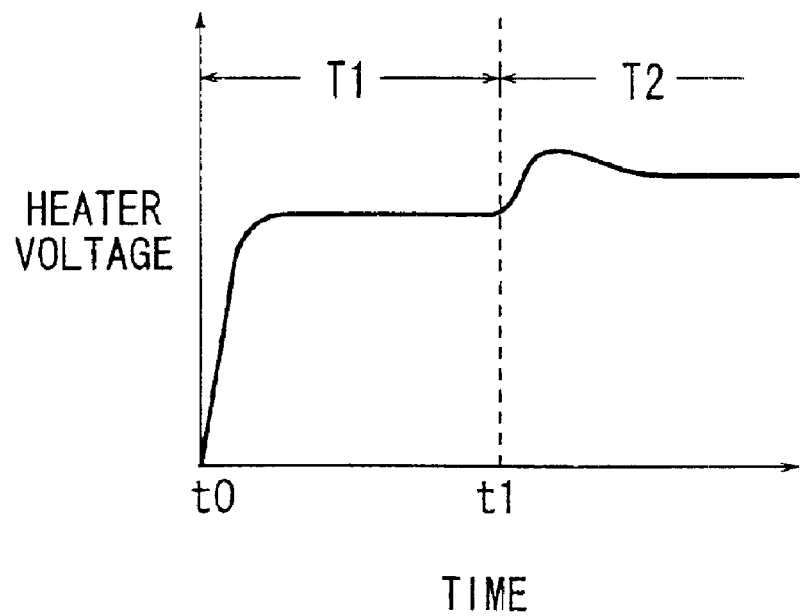
FIG. 9A is a view showing a heater voltage characteristic in the control switching circuit of the first example.
Figure 9B:
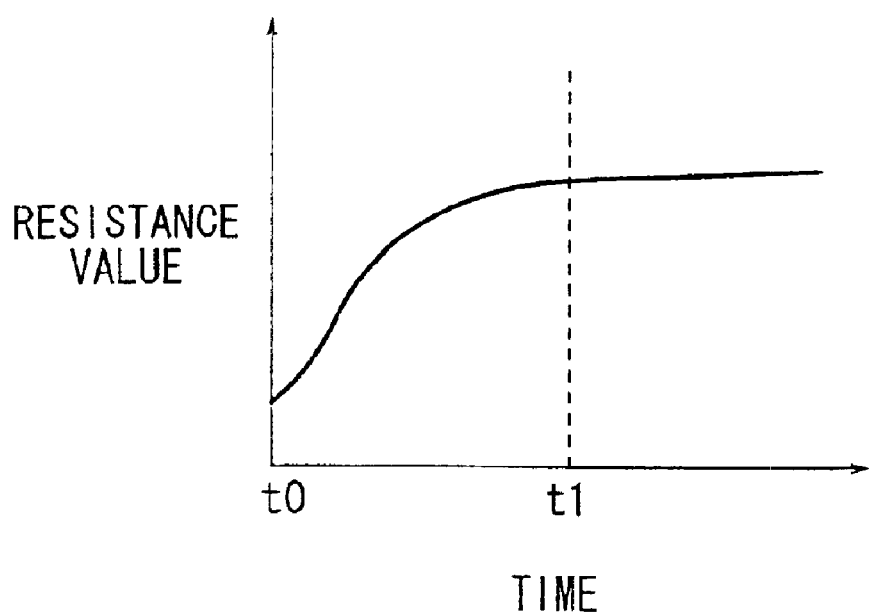
FIG. 9B is a view showing a resistance characteristic in the control switching circuit of the first example.
Figure 10:
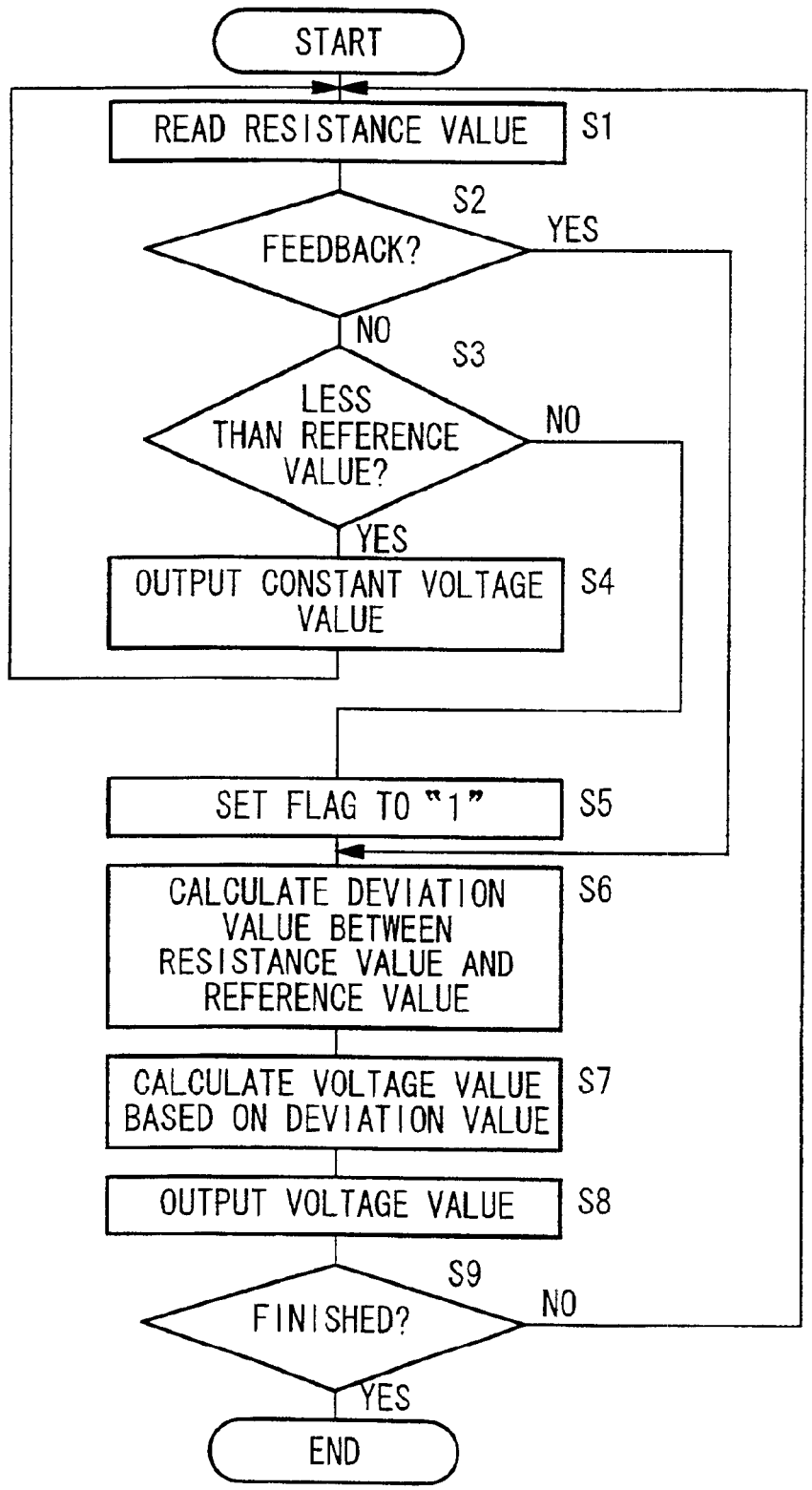
FIG. 10 is a flowchart showing a processing routine of software for carrying out functions of the control switching circuit of the first example.

In the control switching circuit 330A of the first example, as shown in FIGS. 9A, 9B, the constant voltage control is performed during a period T1, i.e., from the time point when heating of the heater 64 is started until the resistance value Dr reaches the reference value Db. When the constant voltage control is performed, the temperature of the heating unit 300 and the resistance value Dr are increased. When the resistance value Dr reaches the reference value Db, i.e., during the period T2 from the time point t1, the feed back control is performed so that the voltage value Dr is kept at the reference value Db.

Functions of the control switching circuit 330A of the first example may be carried out by software executed by a CPU. Next, processing sequence (processing routine) of the software for carrying out the functions of the control switching circuit 330A will be described with reference to FIG. 10.

In step S1, a resistance value Dr is read from the resistance measuring circuit 312. Then, in step S2, it is determined whether feedback control is currently performed or not. For example, it is determined whether a flag indicating feedback control is set to "1".

If it is determined that feedback control is not currently performed, control passes to step S3 for determining whether the read resistance value Dr is less than a reference value Db stored in the resistor 360. If the resistance value Dr is less than the reference value Db, control passes to step S4 for reading a constant voltage value Dc corresponding to resistor 362 to output the constant voltage value Dc to the D/A converter 358. The D/A converter converts the constant voltage value Dc into an analog voltage signal Sv and outputs the voltage signal Sv to the comparator 342. When the process in step S4 is finished, the control passes back to the processing sequence from step S1.

If it is determined that the resistance value Dr is equal to or greater than the reference value Db in step S3, control goes to step S5 for setting the flag indicating feedback control to "1". Thereafter, in step S6, the deviation calculator 352 calculates deviation (difference) between the resistance value Dr from the resistance measuring circuit 312 and the reference value Db from the resistor 360. Then, in step S7, the voltage calculator 354 calculates a voltage value Dv based on the deviation value Dd. In step S8, the voltage calculator 354 outputs the voltage value Dv to the D/A converter 358. The D/A converter 358 converts the voltage value Dv into an analog voltage signal Sv, and outputs the voltage signal Sv to the comparator 342.

Then, in step S9, it is determined whether there is a request for ending the software (interruption of power supply, power reset). If there is no ending request, control passes back to step S1 for repeating the processing sequence from the process of step S1. In this case, since the flag indicating feedback control is set to "1", the control passes to step S6 after step S2, and the process of feedback control is repeated.

As described above, in the gas sensor 10 of the present embodiment, particularly, in the gas sensor 10 having the control switching circuit 330A of the first example, the control mode is switched from constant voltage control to feedback control. Constant voltage control is performed during the period T1 from the time point t1 when heating of the heater 64 is started until the temperature of the substrate 200 reaches a predetermined temperature (until the resistance value Dr of the heating unit 300 reaches the reference value Db). Feedback control is performed after the point t1, so that the temperature of the heater 64 is controlled to keep the predetermined temperature (the reference value Db is used as a target value). Therefore, in the initial heating period, the temperature of the substrate 200 is increased rapidly. Thus, it is possible to reduce the time needed to increase the temperature of the heater 64 to the predetermined temperature.

Next, a control switching circuit 330B of the second example will be described with reference to FIGS. 11 to 14.

In the control switching circuit 330B of the second example, the temperature of the heater 64 is increased rapidly when the temperature of the substrate 200 is low, and the temperature of the heater 64 is increased slowly when the temperature of the substrate 200 is high.

Figure 12:
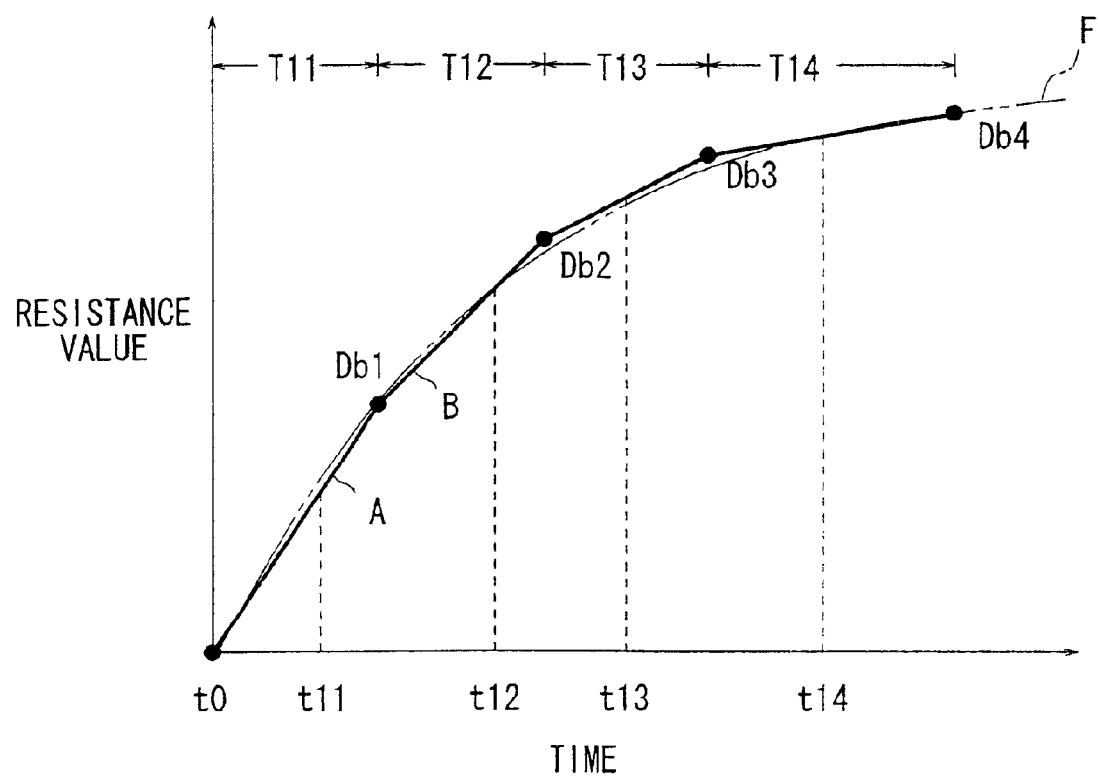
FIG. 12 is a view showing a characteristic of switching control for changing a target resistance value and an increasing rate in multiple heating stages.

Specifically, as shown in FIG. 12, change of the voltage (resistance value) relative to the time passed for increasing the temperature of the heater 64 approximately corresponds to an exponential curve F of first order time-lag function (for example, $y=1-e^{-at}$).

Figure 11:
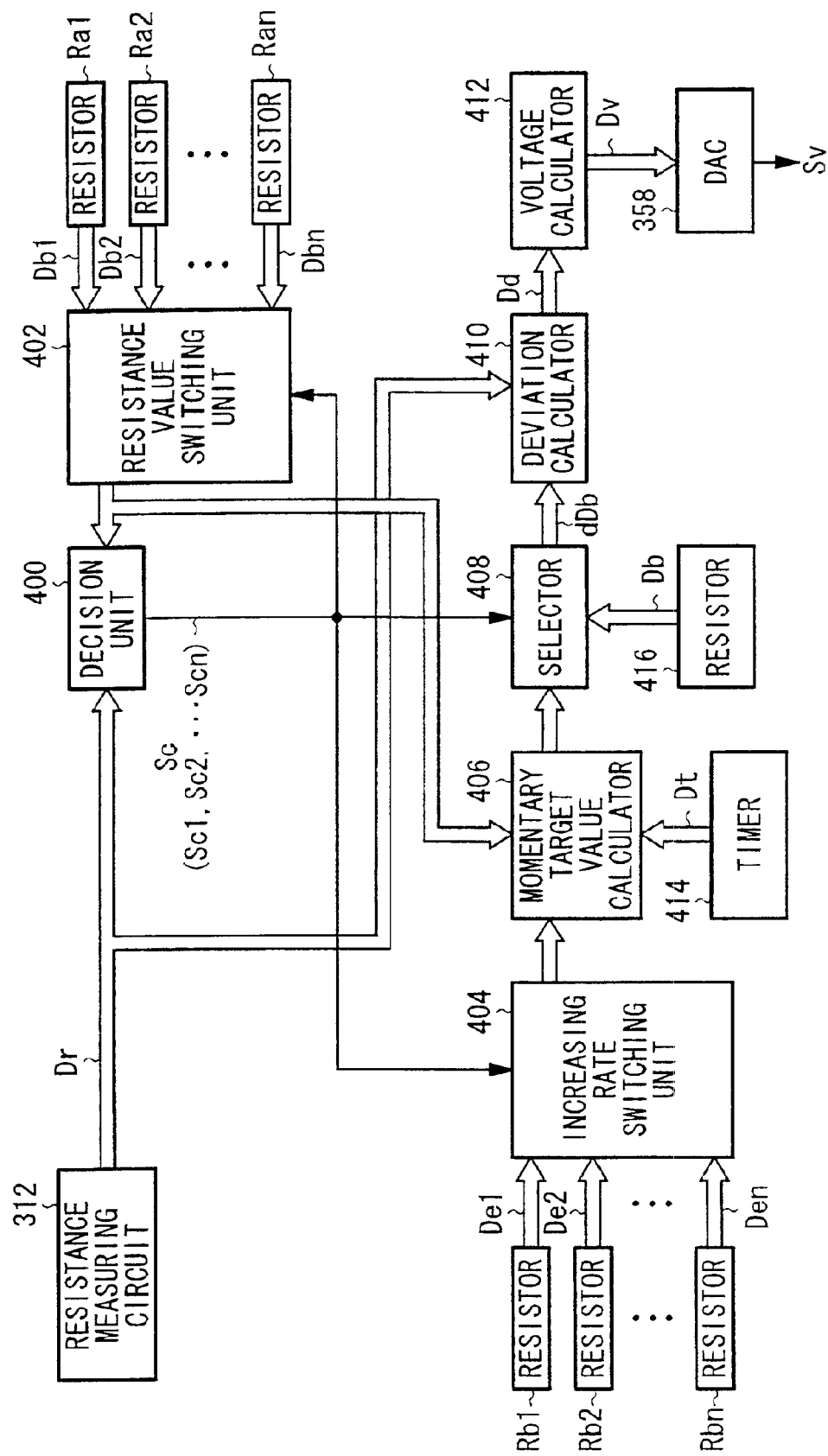
FIG. 11 is a diagram showing an arrangement of a control switching circuit of a second example.

As shown in FIG. 11, the control switching circuit 330B of the second example comprises a decision unit 400, a resistance value switching unit 402, an increasing rate switching unit 404, a momentary target value calculator 406, a selector 408, a deviation calculator 410, a voltage calculator 412, and a D/A converter 358.

The decision unit 400 compares a resistance value Dr from the resistance measuring circuit 312 with resistance values Db1, Db2, . . . , Dbn from the resistance value switching unit 402, respectively. When the resistance value Dr reaches the resistance values Db1, Db2, . . . , Dbn, the decision unit outputs switching signals Sc (Sc1, Sc2, . . . , Scn).

The resistance value switching unit 402 successively outputs the resistance values Db1, Db2, . . . , Dbn corresponding to resistors Ra1, Ra2, . . . , Ran based on input data, i.e., the switching signals Sc (Sc1, Sc2, . . . , Scn) from the decision unit 400. Initially, the resistance value switching unit 402 outputs the resistance value Db1 registered in the resistor Ra1 to the decision unit 400 and the momentary target value calculator 406 irrespective of the input data (switching signal Sc from the decision unit 400).

The increasing rate switching unit 404 successively outputs increasing rates De1, De2, . . . , Den corresponding to resistors Rb1, Rb2, . . . , Rbn based on input data, i.e., the switching signals Sc (Sc1, Sc2, . . . , Scn) from the decision unit 400. Initially, the increasing rate switching unit 404 outputs the initial resistance value De1 corresponding to the resistor Rb1 to the momentary target value calculator 406 irrespective of the input data (switching signal Sc from the decision unit 400).

The momentary target value calculator 406 calculates a current momentary target value dDb based on the resistance value from the resistance value switching unit 402, the increasing rate from the increasing rate switching unit 404, and time information Dt from a timer 414.

Specifically, as shown in FIG. 12, in the first period (first heating stage) T11, the momentary target value calculator 406 calculates a first resistance value changing characteristic (linear line A) of the first period T11 based on an initial value "0", the first resistance value Db1 from the resistance value switching unit 402, and the first increasing rate De1 from the increasing rate switching unit 404. The current momentary target value (at a time point t11, for example) can be calculated easily based on the first resistance value changing characteristic.

In the second period (second heating stage) T12, the momentary target value calculator 406 calculates a second resistance value changing characteristic (linear line B) of the second period T12 based on the first resistance value Db1, the second resistance value Db2 from the resistance value switching unit 402, and the second increasing rate De2 from the increasing rate switching unit 404. The current momentary target value (at a time point t12, for example) can be calculated easily based on the second resistance value changing characteristic.

In the same manner, the third momentary target value of the third period (third heating stage) T13 is easily calculated based on the second resistance value Db2, the third resistance value Db3, the third increasing rate De3, and the current time point (t13). Further, the fourth momentary target value of the fourth period (fourth heating stage) T14 is easily calculated based on the third resistance value Db3, the fourth resistance value Db4, the fourth increasing rate De4, and the current time point (t14).

The selector 408 outputs the momentary target value from the momentary target value calculator 406 to the deviation calculator 410 from a time point t0 when heating of the heater 64 is started until the resistance value Dr of the heating unit 300 reaches the final resistance value Dbn. After the resistance value Dr of the heating unit 300 reaches the final resistance value Dbn, the selector 408 outputs the reference value Db stored in the resistor 416 to the deviation calculator 410.

The deviation calculator 410 calculates the deviation value Dd between the resistance value Dr from the resistance measuring circuit 312 and the momentary target value dDb from the selector 408 or the reference value Db. The voltage calculator 412 calculates the voltage value Dv to be outputted to the comparator 342 based on the deviation value Dd from the deviation calculator 410.

The D/A converter 358 converts the voltage value Dv into an analog signal Sv, and outputs the analog signal Sv to the comparator 342 of the pulse width modulating circuit 334.

Figure 13A:
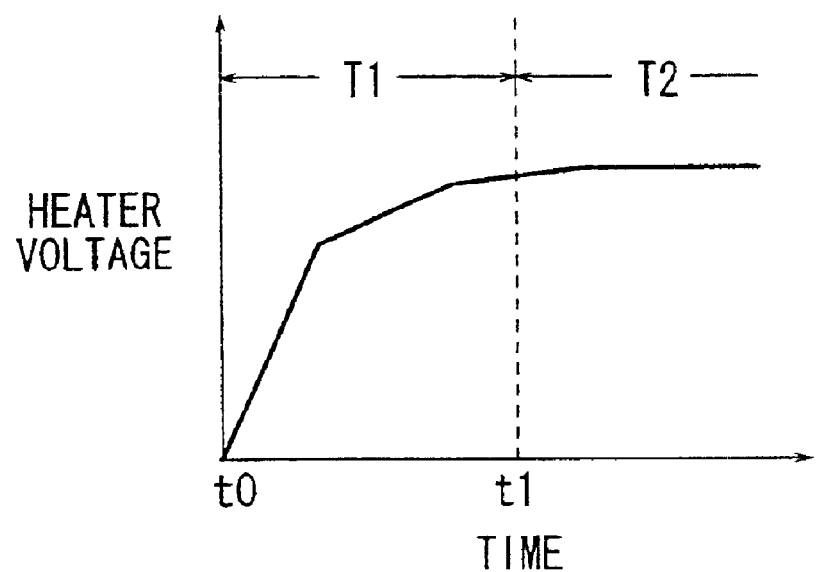
FIG. 13A is a view showing a heater voltage characteristic in the control switching circuit of the second example.
Figure 13B:
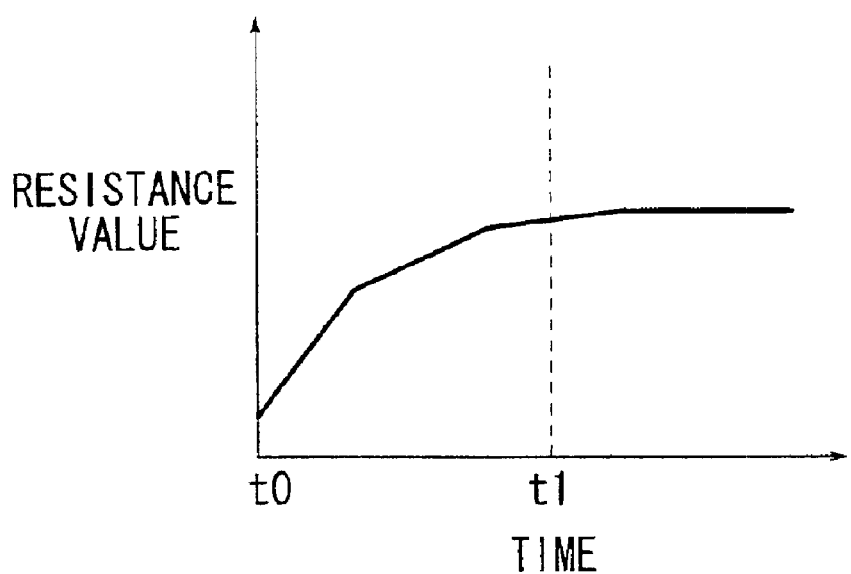
FIG. 13B is a view showing a resistance characteristic in the control switching circuit of the second example.
Figure 14:
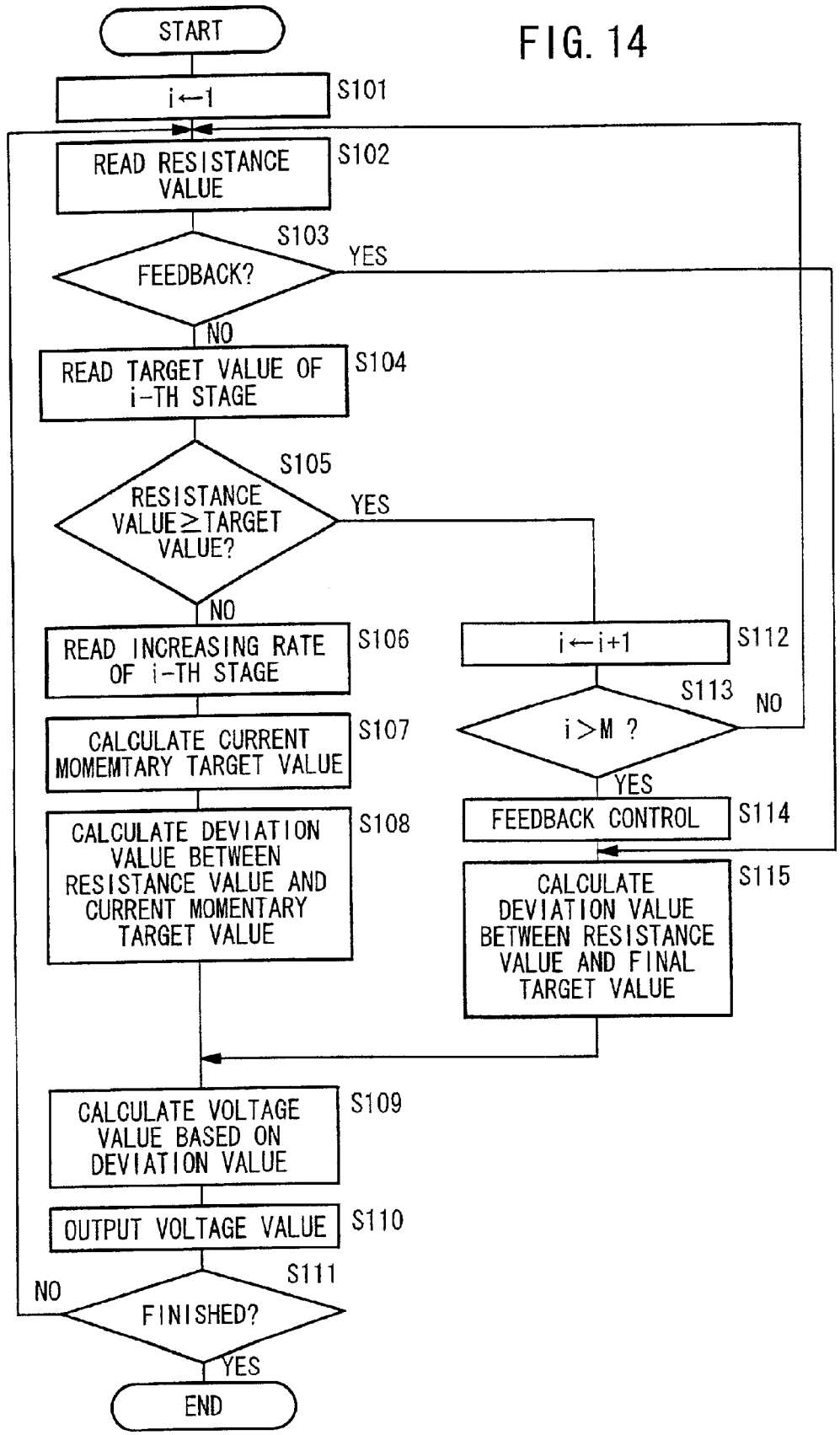
FIG. 14 is a flowchart showing a processing routine of software for carrying out functions of the control switching circuit of the second example.

According to the control switching circuit 330B of the second example, as shown in FIGS. 13A, 13B, the increasing rate is switched step by step in multiple heating stages to control the heater 64 in the period T1 from the time point t0 when heating of the heater 54 is started until the resistance value Dr of the heating unit 300 reaches the reference value Db. With the switching control of the increasing rate performed in multiple stages, the temperature of the heating unit 300 and the resistance value Dr increase gradually. In the period T2 from the time point t1 when the resistance value Dr of the heating unit 300 reaches the reference value Db, feed back control is performed so that the resistance value Dr is kept at the reference value (target value) Db.

In the control switching circuit 330A of the first example, constant voltage control is performed in the first heating stage. Therefore, temperature of the heater 64 increases rapidly, and the control mode can be switched to feedback control in a short period of time.

However, if control mode is switched to feedback control when the temperature of the substrate 200 is high, undesirable heat stress may be applied on the substrate 200 since the increase in the temperature of the heating unit 300 does not stop until the feedback control is actually started. The heat stress may cause formation of cracks in the substrate 200.

Therefore, in the control switching circuit 330B of the second example, the n-th increasing rate Den (the increasing rate of the final stage) is lower than the increasing rate Den−1 (the increasing rate of the stage before the final stage). When the temperature of the substrate 200 is high, the substrate 200 is heated slowly so that the stress (heat stress or the like) applied to the substrate 200 can be reduced. Thus, it is possible to prevent the heater 64 from being heated excessively when the control mode of the heater 64 is switched to the feedback control. Accordingly, it is possible to prevent formation of cracks in the substrate 200.

Preferably, the increasing rates De1, D2e, . . . , Den in respecting heating stages are determined such that the increasing rate becomes low as the resistance value Dr gets closer to the reference value Db. In this case, it is possible to almost stop the increase of the resistance value Dr of the heating unit 300 (the increase of the temperature of the substrate 200) just before the control mode is switched to feedback control. In this manner, the control mode is switched to feedback control smoothly without excessive increase of the temperature.

The increasing rate may be switched twice, three times, or four times. It is because five or more times of switching operations require substantial time and may undesirably prolong the period T1 (from a time point when heating of the heater 64 is started until the control mode is switched to the feedback control).

Preferably, when the temperature of the substrate 200 is 600 degrees centigrade or more, the increasing rates of the resistance value in the respective heating stages are determined such that the temperature of the heater 64 does not increase more than 5 percent of a predetermined temperature (the temperature corresponding to the reference value Db) per second. Specifically, when the temperature of the substrate 200 is 600 degrees centigrade or more, it is preferable that the increasing rates of the respective heating stages are determined such that the temperature of the heater 64 increases at a speed not more than 40 degrees centigrade/sec.

Preferably, when the temperature of the substrate 200 is 500 degrees centigrade or less, the increasing rates of the resistance value in the respective heating stages are determined such that the temperature of the heater 64 increases 1 to 10 percent of the predetermined temperature per second. Specifically, when the temperature of the substrate is 500 degrees centigrade or less, it is preferable that the increasing rates of the respective heating stages are determined that the temperature of the heater 64 increases at a speed more than 20 degrees centigrade/sec., and not more than 100 degrees centigrade/sec.

By determining the desirable increasing rates, it is possible to prevent the substrate 200 to be heated excessively rapidly when the control mode of the heater 64 is switched to the feedback control. Therefore, it is possible to prevent formation of cracks in the substrate 200.

The functions of the control switching circuit 330B of the second example may be carried out by software executed by a CPU. The software for carrying out the functions of the control switching circuit 330B will be explained with reference to FIG. 14.

In step S101, a stage counter i for counting switching stages (heating stages) is set to an initial value "1" to initialize the counter i.

Then, in step S102, a resistance value Dr is read from the resistance measuring circuit 312. Then, in step S103, it is determined whether the current control mode is the feedback control or not. For example, it is determined whether a flag indicating feedback control is set to "1".

If it is determined that feedback control is not currently performed, control passes to step S104 for reading a target value (resistance value) of the i-th stage. Thereafter, in step S105, it is determined whether the resistance value Dr is equal to or greater than the target value of the i-th stage. If the resistance value Dr is less than the target value of the i-th stage, the process of the i-th stage continues. Therefore, control passes to step S106 for reading an increasing rate of the i-th stage.

In step S107, the current momentary target value is calculated based on the target value and the increasing rate of the i-th stage. Then, in step S108, a deviation value between the resistance value Dr and the momentary target value is calculated. Thereafter, in step S109, a voltage value Dv is calculated based on the deviation value. In step S110, the voltage value Dv is outputted to the D/A converter 358. The D/A converter 358 converts the voltage value Dv into an analog voltage signal Sv, and outputs the voltage signal Sv to the comparator 342.

Then, in step S111, it is determined where there is a request for ending the software (interruption of power supply, power reset). If there is no ending request, control passes back step S102 for repeating the processing sequence from the process of step S102.

In step S105, when it is determined that the resistance value Dr is equal to or greater than the target value of the i-th stage, control value passes to step S112 for updating the value of the counter i by +1. Then, in step S113, it is determined whether the process for the final target value is finished or not. Specifically, it is determined whether the value of the counter i is greater than a stage number M or not.

If the value of the counter i is equal to or less than the stage number M, control passes back to step S102 for performing the process of the next stage. When it is determined that the value of the counter is greater than the stage number M, control passes to the next step S114. In step S114, the flag indicating feedback control is set to "1".

Thereafter, in step S115, the deviation value between the resistance value Dr from the resistance measuring circuit 312 and the final target value (reference value Db) is calculated. When the process in step S115 is finished, control passes to step S109 and the subsequent steps, i.e., a voltage value is calculated based on the deviation value, and the voltage value is outputted to the D/A converter 358. Thereafter, the processing sequence from step S109 and the subsequent steps is repeated. Since the feedback control flag is set to "1", control passes to step S115 after step S103 for repeating the processing sequence of the feedback control.

Next, gas sensors of two experiments (first experiment and second experiment) will be explained.

In the first experiment, defective rates F (t) in heating the heater 64 under a certain gas flow condition are plotted in a comparative example 1 and an embodiment 1.

The gas sensor of the comparative example 1 uses the control switching circuit 330A of the first example. The control mode for increasing the temperature of the heater 64 is switched from constant voltage control to feedback control.

The gas sensor of the embodiment 1 uses the control switching circuit 330B of the second example. The temperature of the heater 64 is increased at a speed not more than 40 degrees centigrade/sec. when the temperature of the substrate is 600 degrees centigrade or more. The temperature of the heater 64 is increased at a speed not more than 100 degrees centigrade/sec. when the temperature of the substrate is 500 degrees centigrade or less.

Figure 15:
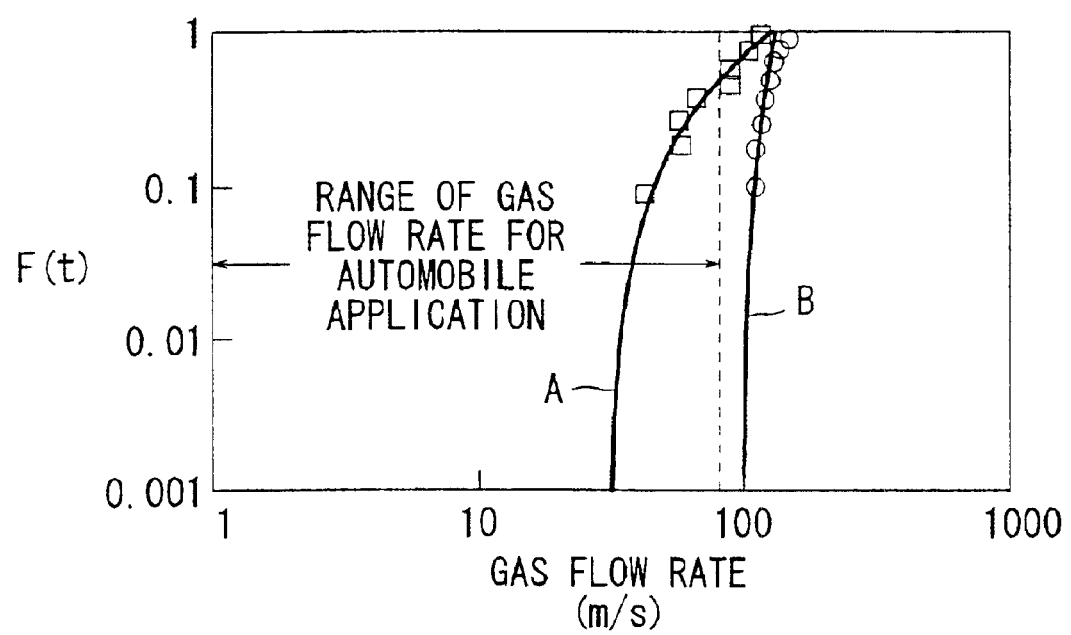
FIG. 15 is a view showing results (change in defective rate relative to change in gas flow rate) of a first experiment.

The range of gas flow rate for the first experiment is determined based on an automobile application. The experiment is performed at a room temperature while changing the gas flow speed by a gas blower. In FIG. 15, results of the comparative example 1 are plotted by squares, and results of the embodiment 1 are plotted by circles. It can be seen that the defective rate of the comparative example 1 is shown by a curve A, and the defective rate of the embodiment 1 is shown by a curve B.

According to the experiment, no formation of cracks is observed in the gas sensor of the embodiment 1 in the range of gas flow rate for the automobile application. In this respect, the gas sensor of the embodiment 1 is advantageous in comparison with the gas sensor of the comparative example 1 in the automobile application.

Next, in the second experiment, controllability for heaters of a gas sensor of a comparative example 2 and a gas sensor of an embodiment 2 in a diesel engine application is tested. The engine speed is changed from 1000 rpm to the 3500 rpm. The relationship between the change of the gas temperature and the change of the temperature of the substrate is examined for each of the gas sensor of the comparative example 2 and the gas sensor of the embodiment 2.

In the comparative example 2, the heater is controlled through two current leads 302A, 302B. In the embodiment 2, the heater is controlled through two current leads 302A, 302B, and an additional voltage measuring lead (for example, voltage measuring lead 316A).

Figure 16:
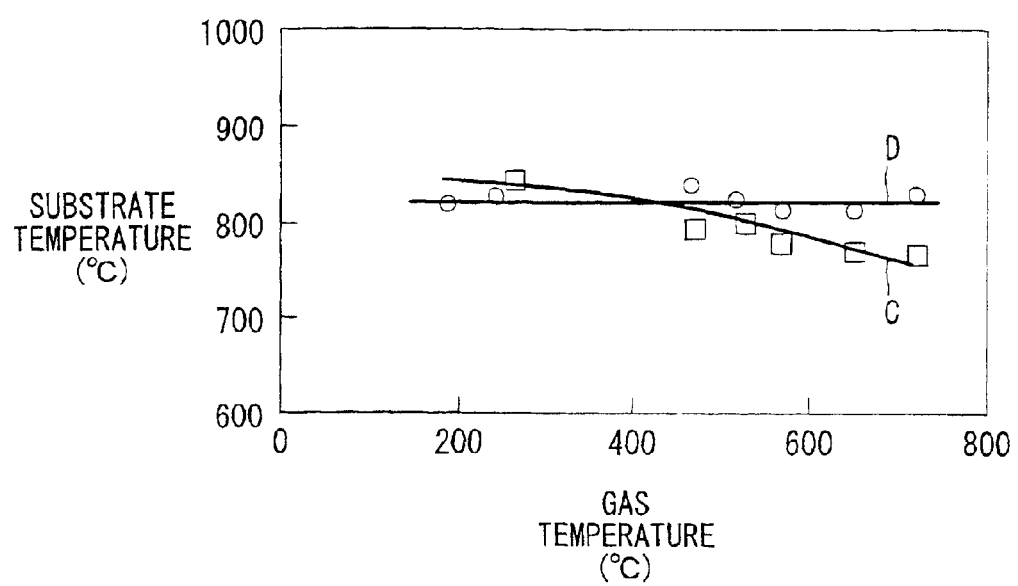
FIG. 16 is a view showing results (change in substrate temperature relative to change in gas temperature) of a second experiment.

In FIG. 16, results of the comparative example 2 are plotted by squares, and results of the embodiment 2 are plotted by circles. It can be seen that the results of the comparative example 2 is shown by a curve C, and the substrate temperature decrease gradually as the increase of the gas temperature. Further, it can be seen that the results of the embodiment 2 is shown by a curve D, and the substrate temperature is kept constant regardless of the change of the gas temperature.

The heater 64 is made up of the heating unit 300 and the current leads 302A, 302B. In the comparative example 2, the resistance of the heater 64 is kept in its entirety. Therefore, when the gas temperature is increased, and the substrate is heated, the temperature (resistance value) of the leads 302A, 302B is increased. Therefore, the temperature (resistance value) of the heating unit 300 is decreased relatively.

In contrast, in the embodiment 2, the gas sensor has the voltage measuring lead (316A, for example). The resistance of the heating unit 300 is directly controlled at a constant value. Therefore, when the substrate is heated and the temperature of the current lead 302A, 302B is increased, the change in the temperature of the substrate 200 is small. Thus, the controllability of the heater 64 is not affected substantially by the change of the gas temperature.

While the invention has been particularly shown and described with reference to preferred embodiments, it will be understood that variations and modifications can be effected thereto by those skilled in the art without departing from the spirit and scope of the invention as defined by the appended claims.

What is claimed is:

1. A method of heating a gas sensor including a ceramic substrate and a heater embedded in said substrate by controlling a temperature of said heater, said method comprising the steps of:

increasing the temperature of said heater at a first rate when the temperature of said substrate is below a predetermined temperature; and increasing the temperature of said heater at a second rate which is lower than said first rate when the temperature of said substrate is above a predetermined temperature.

2. A method according to claim 1, wherein the temperature of said heater is increased at said second rate when the temperature of said substrate is equal to or greater than 600 degrees centigrade.

3. A method according to claim 1, wherein the temperature of said heater is increased at a speed equal to or less than 40 degrees centigrade/sec. when the temperature of said substrate is equal to or greater than 600 degrees centigrade.

4. A method according to claim 1, wherein the temperature of said heater is increased at said first rate when the temperature of said substrate is equal to or less than 500 degrees centigrade.

5. A method according to claim 1, wherein the temperature of said heater is increased at a speed within a range greater than 20 degrees centigrade/sec. but equal to or less than 100 degrees centigrade/sec. when the temperature of said substrate is equal to or less than 500 degrees centigrade.

6. A method according to claim 1, wherein a voltage applied to said heater changes depending on the time passed for increasing the temperature of said heater, according to an exponential curve.

7. A method according to claim 1, wherein said heater has a heating unit, and a resistance of said heating unit is measured and controlled for increasing the temperature of said heater.

8. A gas sensor having a ceramic substrate and a heater embedded in said substrate, said gas sensor comprising:

means for measuring a resistance of a heating unit of said heater; and means for controlling a rate of increasing the resistance of said heating unit per unit time.

9. A gas sensor according to claim 8, wherein said resistance measuring means comprises at least one measuring lead for measuring the resistance of said heating unit.

* * * * *